United States Patent
Commons et al.

[11] Patent Number: 6,049,006
[45] Date of Patent: Apr. 11, 2000

[54] ELEVATION OF HDL CHOLESTEROL BY N-[2-[(AMINOTHIOXOMETHYL) HYDRAZONO]-2-ARYLETHYL]AMIDES

[75] Inventors: Thomas Joseph Commons, Wayne; Susan Christman, Philadelphia, both of Pa.

[73] Assignee: American Home Products Corp., Madison, N.J.

[21] Appl. No.: 09/096,155

[22] Filed: Jun. 11, 1998

Related U.S. Application Data

[60] Provisional application No. 60/049,655, Jun. 16, 1997.

[51] Int. Cl.[7] .................................................. C07C 337/00
[52] U.S. Cl. ................................ 564/19; 560/23; 560/30
[58] Field of Search ............................ 560/23, 30; 564/19

[56] References Cited

U.S. PATENT DOCUMENTS 4,983,755  1/1991  Bühmann et al. ..................... 560/30

FOREIGN PATENT DOCUMENTS 3624349  7/1986  Germany.
3024009  2/1991  Japan.
07149706  6/1995  Japan.

OTHER PUBLICATIONS

Miller et al., *Br. Med. J.*, 282:1741–1744 (1981).
Picardo et al., *Arteriosclerosis.*, 6:434–441 (1986).
Glomset, *J. Lipid Res.*, 9:155–167 (1968).
Glass et al., *Circulation*, vol. 66, Suppl. II 102 (1982).
MacKinnon et al., *J. Biol. Chem.*, 261:2548–2552 (1986).
Grow and Fried, *J. Biol. Chem.*, 253:8034–8041 (1978).
Lagocki and Scanu., *J. Biol. Chem.*, 255:3701–3706 (1978).
Schaefer et al., *J. Lipid Res.* ., 23:1259–1273 (1982).
Tomita et al., *J. Heterocyclic Chem.*, 27:707–710 (1990).
Vega and Grundy, *Current Opinion in Lipidology*, 7:209–216 (1996).
Russ et al., *Am. J. Med.*, 11:480–493 (1951).
Gofman et al., *Circulation*, 34:679–697 (1966).
Miller and Miller, *Lancet*, 1:16–19 (1975).
Gordon et al., *Circulation*, 79:8–15 (1989).
Stampfer et al., *N. England J. Med.*, 325:373–381 (1991).
Badimon et al., *Lab. Invest.*, 60:455–461 (1989).

*Primary Examiner*—Gary L. Kunz
*Assistant Examiner*—Everett White
*Attorney, Agent, or Firm*—Michael R. Nagy

[57] ABSTRACT

This invention relates to the treatment of atherosclerosis via raising the level of HDL cholesterol by administration of a compound of the formula

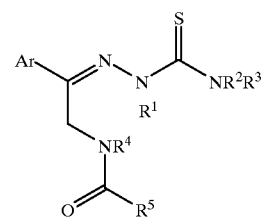

wherein:

$R^1$, $R^2$, and $R^3$ are independently hydrogen, $C_1$–$C_6$ alkyl or —$(CH_2)_{0-6}$Ph where Ph is phenyl optionally substituted by halogen, cyano, nitro, $C_1$–$C_6$ alkyl, $C_1$–$C_6$ alkoxy, trifluoromethyl, $C_1$–$C_6$ alkoxycarbonyl, —$CO_2H$ or OH;

$R^4$ is hydrogen or $C_1$–$C_6$ alkyl;

$R^5$ is hydrogen, $C_1$–$C_6$ alkyl, $C_3$–$C_8$ cycloalkyl, or —$(CH_2)_{0-6}Ar^1$ where $Ar^1$ is phenyl naphthyl, furanyl, pyridinyl or thienyl and $Ar^1$ can be optionally substituted by halogen, cyano, nitro, $C_1$–$C_6$ alkyl, phenyl, $C_1$–$C_6$ alkoxy, phenoxy, tifluoromethyl, $C_1$–$C_6$ alkoxycarbonyl, —$CO_2H$ or OH; and Ar is phenyl, naphthyl, furanyl, pyridinyl or thienyl or Ar is optionally substituted by halogen, cyano, nitro, $C_1$–$C_6$ alkyl, phenyl, $C_1$–$C_6$ alkoxy, phenoxy, tifluoromethyl, $C_1$–$C_6$ alkoxycarbonyl, —$CO_2H$ or OH.

4 Claims, No Drawings

ELEVATION OF HDL CHOLESTEROL BY N-[2-[(AMINOTHIOXOMETHYL) HYDRAZONO]-2-ARYLETHYL]AMIDES

This application claims benefit to priority of provisional patent application Ser. No. 60/049,655 filed on Jun. 16, 1997.

FIELD OF THE INVENTION

This invention relates to compounds useful in elevating high density lipoprotein, the "good" cholesterol. Compounds of this invention increase plasma levels of HDL in a cholesterol fed rat model and as such these compounds may be useful for treating diseases such as atherosclerosis.

BACKGROUND OF THE INVENTION

It is widely believed that HDL is a "protective" lipoprotein [Gloria Lena Vega and Scott Grundy, Current Opinion in Lipidology, 7, 209–216 (1996)] and that increasing plasma levels of HDL may offer a direct protection against the development of atherosclerosis. Numerous studies have demonstrated that both the risk of coronary heart disease (CHD) in humans and the severity of experimental atherosclerosis in animals are inversely correlated with serum HDL cholesterol (HDL-C) concentrations (Russ et al., Am. J. Med. 11 (1951) 480–493; Gofman et al, Circulation, 34 (1966) 679–697; Miller and Miller, Lancet, 1 (1975) 16–19; Gordon et al., Circulation, 79 (1989) 8–15; Stampfer et al., N. Engl. J. Med., 325 (1991) 373–381; Badimon et al., Lab. Invest., 60 (1989) 455–461). Atherosclerosis is the process of accumulation of cholesterol within the arterial wall which results in the occlusion, or stenosis, of coronary and cerebral arterial vessels and subsequent myocardial infarction and stroke. Angiographical studies have shown that elevated levels of some HDL particles in humans appears to be correlated to a decreased number of sites of stenosis in the coronary arteries of humans (Miller et al., Br. Med. J., 282 (1981) 1741–1744).

There are several mechanisms by which HDL may protect against the progression of atherosclerosis. Studies in vitro have shown that HDL is capable of removing cholesterol from cells (Picardo et al., Arteriosclerosis 6 (1986) 434–441). Data of this nature suggest that one antiatherogenic property of HDL may lie in its ability to deplete tissues of excess free cholesterol and eventually lead to the delivery of this cholesterol to the liver (Glomset, J. Lipid Res., 9 (1968) 155–167). This has been supported by experiments showing efficient transfer of cholesterol from HDL to the liver (Glass et al., Circulation, 66 (Suppl. II) (1982) 102; MacKinnon et al., J. Biol. Chem., 261 (1986) 2548–2552). In addition, HDL may serve as a reservoir in the circulation for apoproteins necessary for the rapid metabolism of triglyceride-rich lipoproteins (Grow and Fried, J. Biol. Chem., 253 (1978) 1834–1841; Lagocki and Scanu, J. Biol. Chem., 255 (1980) 3701–3706; Schaefer et al., J. Lipid Res., 23 (1982) 1259–1273). Accordingly, agents which increase HDL cholesterol concentrations are useful as anti-atherosclerotic agents, particularly in the treatment of dyslipoproteinemias and coronary heart disease.

BRIEF DESCRIPTION OF THE INVENTION

The compounds of this invention which elevate plasma levels of HDL cholesterol have the general structure

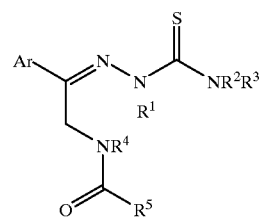

wherein:

$R^1$, $R^2$, and $R^3$ are independently hydrogen, $C_1$–$C_6$ alkyl or —$(CH_2)_{0-6}$Ph where Ph is phenyl optionally substituted by halogen, cyano, nitro, $C_1$–$C_6$ alkyl, $C_1$–$C_6$ alkoxy, trifluoromethyl, $C_1$–$C_6$ alkoxycarbonyl, —$CO_2H$ or OH;

$R^4$ is hydrogen or $C_1$–$C_6$ alkyl;

$R^5$ is hydrogen, $C_1$–$C_6$ alkyl, $C_3$–$C_8$ cycloalkyl, or —$(CH_2)_{0-6}Ar^1$ where $Ar^1$ is phenyl, naphthyl, furanyl, pyridinyl or thienyl and $Ar^1$ can be optionally substituted by halogen, cyano, nitro, $C_1$–$C_6$ alkyl, phenyl, $C_1$–$C_6$ alkoxy, phenoxy, trifluoromethyl, $C_1$–$C_6$ alkoxycarbonyl, —$CO_2H$ or OH; and Ar is phenyl, naphthyl, furanyl, pyridinyl or thienyl or Ar is optionally substituted by halogen, cyano, nitro, $C_1$–$C_6$ alkyl, phenyl, $C_1$–$C_6$ alkoxy, phenoxy, tifluoromethyl, $C_1$–$C_6$ alkoxycarbonyl, —$CO_2H$ or OH. Certain compounds of the above formula where $R^1$, $R^2$ and $R^3$ are hydrogen and $R^5$ is alkyl or phenyl are known to inhibit serum GPT (JP 03024009).

The compounds are tested in vivo in rats fed cholesterol-augmented rodent chow for 8 days according to the test protocol and blood from the rats analyzed for HDL cholesterol.

DETAILED DESCRIPTION OF THE INVENTION

The compounds of this invention are conveniently prepared by the route shown in Scheme I. Specific examples are given in the Experimental Section. These examples are for illustrative purposes only and are not to be construed as limiting to this disclosure in any way. Those skilled in the art will be aware of other methods of preparing compounds of this invention. The starting materials or intermediates are available commercially or can be prepared by standard literature procedures.

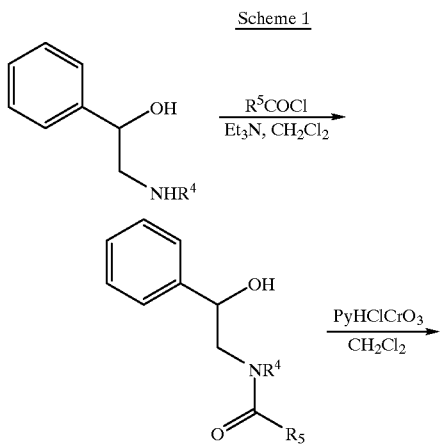

-continued

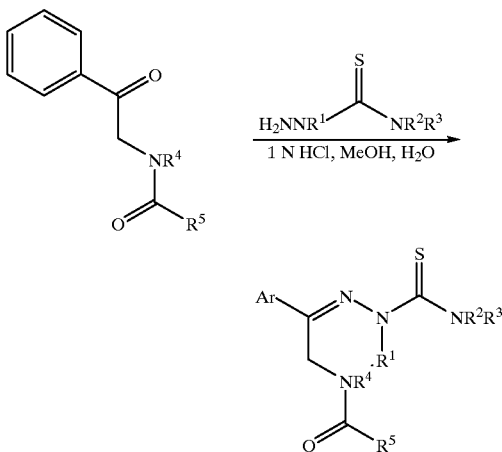

EXAMPLE 1

N-[2-[(Aminothioxomethyl)hydrazono]-2-phenylethyl]acetamide

A solution of acetyl chloride (10 ml, 0.146 moles) in 200 ml of methylene chloride was added under nitrogen dropwise over 45 minutes to a solution of 2-amino-1-phenylethanol (20.0 g, 0.146 moles) and triethylamine (20 ml, 0.146 moles) in 300 ml of methylene chloride at ice bath temperature. After the addition the reaction was stirred at ice bath temperature for 3 hours and overnight at room temperature. The reaction was extracted with 1N HCl. The organic layer was separated and the aqueous layer was extracted with methylene chloride and then 10% methanol-methylene chloride. The organic extracts were combined, dried (MgSO$_4$) and the solvent removed under reduced pressure to give a solid material. Recrystallization of this solid from isopropyl alcohol gave N-(2-hydroxy-2-phenyl-ethyl)-acetamide (9.0 g, 34%) as a white solid, mp 120–122° C.

Elemental Analysis for $C_{10}H_{13}NO_2$

Calc'd: C, 67.02; H, 7.31; N, 7.82

Found: C, 66.95; H, 7.28; N, 8.05

A mixture of N-(2-hydroxy-2-phenyl-ethyl)-acetamide (7.68 g, 43 mmol), prepared in the previous step, and pyridinium chlorochromate (14.0 g, 65 mmol) in 800 ml of methylene chloride was stirred at room temperature for 5 hours. The organic phase was decanted from a black oily residue in the flask. This black residue was triturated with methylene chloride and then with 10% methanol-methylene chloride. The organic phases were concentrated under reduced pressure and the residue chromatographed on 400 g of silica gel (230–400 mesh) using ethyl acetate-methylene chloride as the eluent. Isolation of the desired component gave N-(2-oxo-2-phenyl-ethyl)-acetamide (4.0 g, 53%) as a white solid. The material was used in the following reaction without additional purification, MS m/e (M+H)$^+$178.

Thiosemicarbazide (1.98 g, 20 mmol) was added to a solution of N-(2-oxo-2-phenyl-ethyl)-acetamide (3.84 g, 20 mmol, prepared in the previous step, in 70 ml of methanol plus 5.4 ml of 1N HCl plus 5.0 ml of water and the reaction stirred at room temperature overnight. The solid formed was collected by filtration and dried to give 3.9 g (78%) of the title compound as a white solid, mp 208–211° C.

Elemental Analysis for $C_{11}H_{14}N_4OS$

Calc'd: C, 52.78; H, 5.64; N, 22.38

Found: C, 52.52; H, 5.60; N, 22.57

EXAMPLE 2

N-[2-[(Aminothioxomethyl)hydrazono]-2-phenylethyl]cyclohexanecarboxamide

A solution of cyclohexanecarbonyl chloride (19.5 ml, 0.146 moles) in 200 ml of methylene chloride was added under nitrogen dropwise over approximately 1 hour to a solution of 2-amino-1-phenylethanol (20.0 g, 0.146 moles) and triethylamine (20.0 ml, 0.146 moles) in 300 ml of methylene chloride at ice bath temperature. After the addition the reaction was stirred at ice bath temperature for 2 hours and then at room temperature for approximately 1.5 hours. The reaction was extracted with 1N HCl, dried (MgSO$_4$) and the solvent removed under reduced pressure to give 25.0 g of a tan solid. Recrystallization of the solid from isopropyl alcohol gave cyclohexane carboxylic acid (2-hydroxy-2-phenyl-ethyl)amide (15.34 g, 42%) as a white solid, mp 118–119° C.

Elemental Analysis for $C_{15}H_{21}NO_2$

Calc'd: C, 72.84; H, 8.56; N, 5.66

Found: C, 73.13; H, 8.59; N, 5.82

A mixture of cyclohexane carboxylic acid (2-hydroxy-2-phenyl-ethyl)amide (14.0 g, 56.6 mmol), prepared in the previous step, and pyridinium chlorochromate (18.36 g, 84.9 mmol) in 500 ml of methylene chloride was stirred at room temperature for 4 hours. The reaction was filtered and the black residue was rinsed multiple times with methylene chloride and then one time with methanol. The combined filtrates were concentrated under reduced pressure to give 21.04 g of a brown solid. Purification of the solid by column chromatography on 300 g of silica gel (230–400 mesh) using ethyl acetate-methylene chloride as the eluent gave 3.76 g (27%) of a light green solid. Recrystallization of the solid from isopropyl alcohol gave cyclohexane carboxylic acid (2-oxo-2-phenyl-ethyl)amide as a white solid, mp 114–115° C.

Elemental Analysis for $C_{15}H_{19}NO_2$

Calc'd: C, 73.44; H, 7.81; N, 5.71

Found: C, 72.65; H, 7.95; N, 5.67

Thiosemicarbazide (2.23 g, 24.5 mmol) was added to a solution of cyclohexane carboxylic acid (2-oxo-2-phenyl-ethyl)-amide (6.0 g, 24.5 mmol), prepared in the previous step, in 87 ml of methanol plus 6.75 ml of 1N HCl plus 6.25 ml of water and the reaction stirred at room temperature for 4 days. The solvent was removed under reduced pressure to give 8.2 g of a green oil which was chromatographed on 400 g of silica gel (230–400 mesh) using ethyl acetate-methylene chloride as the eluent. The material isolated was recrystallized from isopropyl alcohol to give the title compound (3.55 g, 46%) as a white solid, mp 104–110° C.

Elemental Analysis for $C_{16}H_{22}N_4OS$

Calc'd: C, 60.19; H, 7.07; N, 17.20

Found: C, 59.70; H, 7.10; N, 16.87

EXAMPLE 3

N-[2-[(Aminothioxomethyl)hydrazono]-2-phenylethyl]benzamide

A solution of benzoyl chloride (16.9 ml, 0.146 moles) in 200 ml of methylene chloride was added under nitrogen dropwise over approximately 1 hour to a solution of 2-amino-1-phenylethanol (20.0 g, 0.146 moles) and triethylamine (20.0 ml, 0.146 moles) in 300 ml of methylene chloride at ice bath temperature. After the addition the reaction was stirred at ice bath temperature for 2 hours and then at room temperature for approximately 2 hours. The solid formed was collected by filtration and dried to give N-(2-hydroxy-2-phenyl-ethyl)-benzamide (20.33 g, 58%) as a white solid, mp 140–143° C.

Elemental Analysis for $C_{15}H_{15}NO_2$

Calc'd: C, 74.67; H, 6.27; N, 5.81

Found: C, 74.83; H, 6.47; N, 5.85

In the same manner as described in Step 2 of Example 2, N-(2-oxo-2-phenyl-ethyl)-benzamide (8.25 g, 83%) was obtained as a white solid, mp 114–120° C. The material was not stable and therefore immediately used in the following reaction.

Thiosemicarbazide (1.33 g, 14.6 mmol) was added to a solution of N-(2-oxo-2-phenyl-ethyl)-benzamide (3.5 g, 14.6 mmol), prepared in the previous step, in 53 ml of methanol plus 4 ml of 1N HCl plus 3.75 ml of water and the reaction stirred at room temperature overnight. The solvent was removed under reduced pressure to give 5.0 g of an off-white solid. Recrystallization of this solid from isopropyl alcohol gave the title compound (3.64 g, 80%) as a white solid, mp 171–172° C.

Elemental Analysis for $C_{16}H_{16}N_4OS$

Calc'd: C, 61.52; H, 5.16; N, 17.93

Found: C, 61.27; H, 5.23; N, 17.93

EXAMPLE 4

N-[2-[(Aminothioxomethyl)-hydrazono]-2-phenylethyl]-2-methyl-propanamide

In the same manner as described in Step 1 of Example 2 where 2-methylpropionyl chloride is substituted for cyclohexanecarbonyl chloride, N-(2-hydroxy-2-phenyl-ethyl)-2-methyl-propanamide (17.93 g, 79%) was obtained as an off-white solid mp 75–77° C.

Elemental Analysis for $C_{12}H_{17}NO_2$

Calc'd: C, 69.53; H, 8.27; N, 6.76

Found: C, 69.65; H, 8.19; N, 6.75

A mixture of N-(2-hydroxy-2-phenyl-ethyl)-2-methyl-propanamide (15.0 g, 72 mmol), prepared in the previous step, and pyridinium chlorochromate (23.7 g, 110 mmol) in 300 ml of methylene chloride was stirred at room temperature for 5 hours. The reaction was filtered and the filtrate concentrated under reduced pressure to give a dark residue. Chromatography of the residue on silica gel (230–400 mesh) using ethyl acetate-methylene chloride as the eluent gave N-(2-oxo-phenyl-ethyl)-2-methyl-propanamide (6.07 g, 41%) as a light green solid, mp 88–93° C.

Elemental Analysis for $C_{12}H_{15}NO_2$

Calc'd: C, 70.22; H, 7.37; N, 6.82

Found: C, 69.12; H, 7.36; N, 6.95

Thiosemicarbazide (2.22 g, 24.4 mmol) was added to a solution of N-(2-oxo-phenyl-ethyl)-2-methyl-propanamide (5.0 g, 24.4 mmol), prepared in the previous step, in 70 ml of methanol plus 6.75 ml of 1N HCl plus 6.25 ml of water and the reaction stirred at room temperature overnight. The solid formed was collected by filtration, rinsed with isopropyl alcohol and hexane, and then dried to give 4.12 g of a white solid. Recrystallization of this solid from isopropyl alcohol gave the title compound (3.15 g, 46%) as a white solid, mp 183–185° C.

Elemental Analysis for $C_{13}H_{18}N_4OS$

Calc'd: C, 56.09; H, 6.52; N, 20.13

Found: C, 56.01; H, 6.61; N, 20.09

EXAMPLE 5

2-[2-(Benzylcarbonylamino)-1-phenyl-ethylidene]-hydrazinecarbothioamide

In the same manner as described in Step 1 of Example 1, substituting phenylacetyl chloride for acetyl chloride, N-(2-hydroxy-2-phenyl-ethyl)-2-phenyl-acetamide (36 g, 96%) was obtained as a white solid, mp 97–99° C.

Elemental Analysis for $C_{16}H_{17}NO_2$

Calc'd: C, 75.27; H, 6.71; N, 5.49

Found: C, 75.09; H, 6.61; N, 5.37

In the same manner as described in Step 2 of Example 4, N-(2-oxo-2-phenyl-ethyl)-2-phenyl-acetamide (4.32 g, 55%) was obtained as an unstable green solid, mp 66–77° C. The material was immediately used in the following reaction.

In the same manner as described in Step 3 of Example 4, the title compound was obtained as an off-white solid, mp 170–172° C.

Elemental Analysis for $C_{17}H_{18}N_4OS$

Calc'd: C, 62.53; H, 5.62; N, 17.04

Found: C, 62.07; H, 5.59; N, 16.80

EXAMPLE 6

2-Methyl-N-[2-[[methylamino]thioxomethyl]hydrazono]-2-phenylethyl]propanamide

Thiosemicarbazide (2.1 g, 20 mmol) was added to a solution of N-(2-oxo-phenylethyl)-2-methyl-propanamide (3.0 g, 14.6 mmol), prepared in Step 2 of Example 4, in 40 ml of methanol plus 4 ml of 1N HCl plus 3.7 ml of water and the reaction stirred at room temperature overnight. The solvent was removed under reduced pressure. The residue was taken up in methylene chloride, washed multiple times with water, dried ($MgSO_4$) and the solvent removed under reduced pressure to give 2.44 g of a white solid. Recrystallization of the solid from isopropyl alcohol gave the title compound (1.9 g, 45%) as a white solid, mp 172–173° C.

Elemental Analysis for $C_{14}H_{20}N_4OS$

Calc'd: C, 57.51; H, 6.89; N, 19.16

Found: C, 57.24; H, 6.83; N, 19.18

PHARMACOLOGY

In Vivo Assay: Male Sprague-Dawley rats weighing 200–225 g are housed two per cage and fed Purina Rodent Chow Special Mix 5001-S supplemented with 0.25% cholic acid and 1.0% cholesterol and water ad libitum for 8 days. Each test substance is administered to a group of six rats fed the same diet with the test diet mixed in as 0.005–0.1% of the total diet. Body weight and food consumption are recorded prior to diet administration and at termination. Typical doses of the test substances are 5–100 mg/kg/day.

At termination, blood is collected from anesthetized rats and the serum is separated by centrifugation. Total serum cholesterol is assayed using the Sigma Diagnostics enzymatic kit for the determination of cholesterol, Procedure No. 352, modified for use with ninety-six well microtiter plates. After reconstitution with water the reagent contains 300 U/l cholesterol oxidase, 100 U/l horse radish peroxidase, 0.3 mmoles/14-aminoantipyrine and 30.0 mmoles/1 p-hydroxybenzenesulfonate in a pH 6.5 buffer. In the reaction cholesterol is oxidized to produce hydrogen peroxide which is used to form a quinoneimine dye. The concentration of dye formed is measured spectrophotomtrically by absorbance at 490 nm after incubation at 25° C. for 30 minutes. The concentration of cholesterol was determined for each serum sample relative to a commercial standard from Sigma.

HDL cholesterol concentrations in serum are determined by separation of lipoprotein classes by fast protein liquid chromatography (FPLC) by a modification of the method of Kieft et al., J. Lipid Res., 32 (1991) 859–866. 25 μl of serum is injected onto Superose 12 and Superose 6 (Pharmacia), in series, with a column buffer of 0.05M Tris (2-amino-2-hydroxymethyl-1,3-propanediol) and 0.15M sodium chloride at a flow rate of 0.5 ml/min. The eluted sample is mixed on line with Boehringer-Mannheim cholesterol reagent pumped at 0.2 ml/min. The combined eluents are mixed and incubated on line through a knitted coil (Applied Biosciences) maintained at a temperature of 45° C. The eluent is monitored by measuring absorbance at 490 nm and gives a continuous absorbance signal proportional to the cholesterol concentration. The relative concentration of each lipoprotein class is calculated as the per cent of total absorbance. HDL cholesterol concentration, in serum, is calculated as the per cent of total cholesterol as determined by FPLC multiplied by the total serum cholesterol concentration.

TABLE I

Cholesterol Fed Rat

| Example | % Increase in HDL (Dose) |
|---|---|
| Example 1 | 118.4% (100 mg/kg) |
| Example 2 | 78.9% (100 mg/kg) |
| Example 3 | 25.8% (100 mg/kg) |
| Example 4 | 155.5% (100 mg/kg) |
| Example 5 | 43% (100 mg/kg) |
| Example 6 | 42.4% (90 mg/kg) |

PHARMACEUTICAL COMPOSITION

Compounds of this invention may be administered neat or with a pharmaceutical carrier to a patient in need thereof. The pharmaceutical carrier may be solid or liquid.

Applicable solid carriers can include one or more substances which may also act as flavoring agents, lubricants, solubilizers, suspending agents, fillers, glidants, compression aids, binders or tablet-disintegrating agents or an encapsulating material. In powders, the carrier is a finely divided solid which is in admixture with the finely divided active ingredient. In tablets, the active ingredient is mixed with a carrier having the necessary compression properties. In suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such a solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water particularly containing additives as above, e.g., cellulose derivatives, preferable sodium carboxymethyl cellulose solution), alcohols (including monohydric alcohols and polyhydric alcohols, e.g., glycols) and their derivatives, and oils (e.g., fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

The compounds of this invention may be administered rectally in the form of a conventional suppository. For administration by intranasal or intrabronchial inhalation or insufflation, the compounds of this invention may be formulated into an aqueous or partially aqueous solution, which can then be utilized in the form of an aerosol. The compounds of this invention may also be administered transdermally through the use of a transdermal patch containing the active compound and a carrier that is inert to the active compound, is non-toxic to the skin, and allows delivery of the agent for systemic absorption into the blood stream via the skin. The carrier may take any number of forms such as creams and ointments, pastes, gels, and occlusive devices. The creams and ointments may be viscous liquid or semi-solid emulsions of either the oil in water or water in oil type. Pastes comprised of absorptive powders dispersed in petroleum or hydrophilic petroleum containing the active ingredient may also be suitable. A variety of occlusive devices may be used to release the active ingredient into the blood stream such as a semipermeable membrane covering a reservoir containing the active ingredient with or without a carrier, or a matrix containing the active ingredient. Other occlusive devices are known in the literature.

The dosage to be used in the treatment of a specific patient suffering from high density lipoprotein insufficiency must be subjectively determined by the attending physician. The variables involved include the severity of the dysfunction, and the size, age, and response pattern of the patient. Treatment will generally be initiated with small dosages less than the optimum dose of the compound. Thereafter the dosage is increased until the optimum effect under the circumstances is reached. Precise dosages for oral or parenteral administration will be determined by the administering physician based on experience with the individual subject treated and standard medical principles.

Preferably the pharmaceutical composition is in unit dosage form, e.g., as tablets or capsules. In such form, the composition is sub-divided in unit doses containing appropriate quantities of the active ingredient; the unit dosage form can be packaged compositions, for example packed powders, vials, ampoules, prefilled syringes or sachets containing liquids. The unit dosage form can be, for example, a capsule or tablet itself, or it can be the appropriate number of any such compositions in package form.

What is claimed is:
1. A compound of the formula:

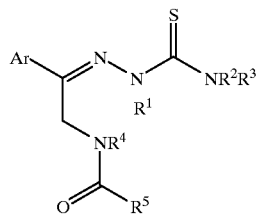

wherein:
- $R^1$, $R^2$, and $R^3$ are independently hydrogen, or $C_1$–$C_6$ alkyl;
- $R^4$ is hydrogen or $C_1$–$C_6$ alkyl;
- And when $R^1$, $R^2$, and $R^3$ are all hydrogen, $R^5$ is $C_3$–$C_8$ cycloalkyl, or —$(CH_2)_n Ar^1$ where n is 1–6, and when one or $R^1$, $R^2$, and $R^3$ is not hydrogen, $R^5$ is hydrogen, $C_1$–$C_6$ alkyl, $C_3$–$C_8$ cycloalkyl or —$(CH_2)_n Ar^1$ where n is 0–6, wherein $Ar^1$ is phenyl, naphthyl, furanyl, pyridinyl or thienyl and $Ar^1$ is optionally substituted by halogen, cyano, nitro, $C_1$–$C_6$ alkyl, phenyl, $C_1$–$C_6$ alkoxy, phenoxy, trifluoromethyl, $C_1$–$C_6$ alkoxycarbonyl, —$CO_2H$ or OH; and
- Ar is phenyl, naphthyl, furanyl, pyridinyl or thienyl where Ar is optionally substituted by halogen, cyano, nitro, $C_1$–$C_6$ alkyl, phenyl, $C_1$–$C_6$ alkoxy, phenoxy, trifluoromethyl, $C_1$–$C_6$ alkoxycarbonyl, —$CO_2H$ or OH.

2. A compound according to claim 1 which is N-[2-[(aminothioxomethyl)hydrazono]-2-phenylethyl]cyclohexanecarboxamide.

3. A compound according to claim 1 which is 2-[2-(benzylcarbonylamino)-1-phenylethylidene]-hydrazinecarbothioamide.

4. A compound according to claim 1 which is 2-methyl-N-[2-[[methylamino]thioxomethyl]hydrazono]-2-phenylethyl]propanamide.

* * * * *